United States Patent
Ziolo et al.

(10) Patent No.: US 7,527,640 B2
(45) Date of Patent: May 5, 2009

(54) BONE FIXATION SYSTEM

(75) Inventors: Tara Ziolo, Boonton, NJ (US);
Takkwong R Leung, Piscataway, NJ (US)

(73) Assignee: EBI, LLC, Parsippany, NJ (US)

(*) Notice: Subject to any disclaimer, the term of this patent is extended or adjusted under 35 U.S.C. 154(b) by 761 days.

(21) Appl. No.: 11/023,096

(22) Filed: Dec. 22, 2004

(65) Prior Publication Data

US 2006/0149251 A1   Jul. 6, 2006

(51) Int. Cl.
*A61B 17/56* (2006.01)
*A61B 17/58* (2006.01)

(52) U.S. Cl. ............................ 606/288; 606/246

(58) Field of Classification Search ............ 606/69, 606/280, 70, 71, 906, 286–291, 295, 296, 606/305–308, 319, 267–269, 272; 411/402, 411/403, 396, 537
See application file for complete search history.

(56) References Cited

U.S. PATENT DOCUMENTS

| | | | |
|---|---|---|---|
| 2,248,054 A | 7/1941 | Decker | |
| 2,293,930 A | 8/1942 | Braendel | |
| 2,362,741 A * | 11/1944 | Berke | 606/54 |
| 2,580,821 A | 1/1952 | Nicola | |
| 2,780,223 A | 2/1957 | Haggland | |
| 3,741,205 A | 6/1973 | Markolf et al. | |
| 3,940,946 A * | 3/1976 | Andersen | 464/89 |
| 4,279,249 A | 7/1981 | Vert et al. | |
| 4,388,921 A | 6/1983 | Sutter et al. | |
| 4,473,068 A | 9/1984 | Oh | |
| 4,484,570 A | 11/1984 | Sutter et al. | |
| 4,655,203 A | 4/1987 | Törmälä et al. | |
| 4,743,257 A | 5/1988 | Törmälä et al. | |
| 4,860,513 A * | 8/1989 | Whitman | 52/410 |
| 4,903,691 A | 2/1990 | Heinl | |
| 4,905,680 A | 3/1990 | Tunc | |
| 5,053,036 A | 10/1991 | Perren et al. | |
| 5,057,109 A | 10/1991 | Olerud | |
| 5,069,569 A * | 12/1991 | Lieser | 403/57 |
| 5,080,665 A | 1/1992 | Jarrett et al. | |
| 5,108,399 A | 4/1992 | Eitenmuller et al. | |
| 5,129,903 A | 7/1992 | Luhr et al. | |
| 5,139,498 A | 8/1992 | Astudillo Ley | |
| 5,147,360 A | 9/1992 | Dubousset | |
| 5,180,381 A | 1/1993 | Aust et al. | |
| 5,290,281 A | 3/1994 | Tschakaloff | |

(Continued)

FOREIGN PATENT DOCUMENTS

EP   1 570 796   9/2005

OTHER PUBLICATIONS

Partial European Search Report.

*Primary Examiner*—Eduardo C Robert
*Assistant Examiner*—Ellen Rust
(74) *Attorney, Agent, or Firm*—Harness, Dickey & Pierce, P.L.C.

(57) ABSTRACT

A bone fixation system. The bone fixation system includes a fixation plate including at least one fixation hole, and at least one fastener, the fastener including a coupler and a shank for engaging a bone. The coupler is threadably engaged with the fixation hole. The shank is angulatably retained by the coupler and orientable relative to the fixation plate at a selectable angle.

9 Claims, 3 Drawing Sheets

U.S. PATENT DOCUMENTS

| | | | |
|---|---|---|---|
| 5,326,206 A * | 7/1994 | Moore | 411/113 |
| 5,346,492 A | 9/1994 | Morgan | |
| 5,364,399 A | 11/1994 | Lowery et al. | |
| 5,376,102 A | 12/1994 | Jarrett et al. | |
| 5,423,826 A | 6/1995 | Coates et al. | |
| 5,468,242 A | 11/1995 | Reisberg | |
| 5,520,690 A | 5/1996 | Errico et al. | 606/61 |
| 5,531,746 A * | 7/1996 | Errico et al. | 606/287 |
| 5,534,032 A * | 7/1996 | Hodorek | 623/20.32 |
| 5,569,250 A | 10/1996 | Sarver et al. | |
| 5,578,034 A | 11/1996 | Estes | |
| 5,578,046 A | 11/1996 | Liu et al. | |
| 5,601,553 A | 2/1997 | Trebing et al. | |
| 5,607,426 A * | 3/1997 | Ralph et al. | 606/287 |
| 5,607,427 A | 3/1997 | Tschakaloff | |
| 5,607,428 A | 3/1997 | Lin | |
| 5,676,666 A | 10/1997 | Oxland et al. | |
| 5,681,311 A | 10/1997 | Foley et al. | |
| 5,690,631 A | 11/1997 | Duncan | |
| 5,702,396 A | 12/1997 | Hoenig et al. | |
| 5,704,936 A | 1/1998 | Mazel | |
| 5,707,372 A | 1/1998 | Errico et al. | |
| 5,709,686 A | 1/1998 | Talos et al. | |
| 5,713,898 A | 2/1998 | Stücker et al. | |
| 5,713,900 A | 2/1998 | Benzel et al. | |
| 5,716,279 A * | 2/1998 | Ham et al. | 464/159 |
| 5,718,705 A | 2/1998 | Sammarco | |
| 5,735,853 A | 4/1998 | Olerud | |
| 5,766,176 A | 6/1998 | Duncan | |
| 5,797,914 A | 8/1998 | Leibinger | |
| 5,800,433 A | 9/1998 | Benzel et al. | |
| 5,814,048 A | 9/1998 | Morgan | |
| 5,833,418 A * | 11/1998 | Shoji | 411/396 |
| 5,843,082 A | 12/1998 | Yuan et al. | |
| 5,868,746 A | 2/1999 | Sarver et al. | |
| 5,876,402 A | 3/1999 | Errico et al. | |
| 5,904,683 A * | 5/1999 | Pohndorf et al. | 606/287 |
| 5,925,048 A | 7/1999 | Ahmad et al. | |
| 5,954,722 A | 9/1999 | Bono | |
| 5,961,524 A | 10/1999 | Crombie | |
| 5,980,540 A | 11/1999 | Bruce | |
| 6,001,101 A * | 12/1999 | Augagneur et al. | 606/73 |
| 6,019,763 A | 2/2000 | Nakamura et al. | |
| 6,036,693 A | 3/2000 | Yuan et al. | |
| 6,039,740 A | 3/2000 | Olerud | |
| 6,090,111 A | 7/2000 | Nichols | |
| 6,117,173 A | 9/2000 | Taddia et al. | |
| 6,129,730 A | 10/2000 | Bono et al. | |
| 6,147,135 A | 11/2000 | Yuan et al. | |
| 6,152,927 A | 11/2000 | Farris et al. | |
| 6,179,839 B1 | 1/2001 | Weiss et al. | |
| 6,193,721 B1 | 2/2001 | Michelson | |
| 6,206,881 B1 | 3/2001 | Frigg et al. | |
| 6,206,883 B1 | 3/2001 | Tunc | |
| 6,214,008 B1 | 4/2001 | Illi | |
| 6,221,075 B1 | 4/2001 | Törmälä et al. | |
| 6,228,085 B1 | 5/2001 | Theken et al. | |
| 6,235,033 B1 * | 5/2001 | Brace et al. | 606/69 |
| 6,241,771 B1 | 6/2001 | Gresser et al. | |
| 6,261,291 B1 * | 7/2001 | Talaber et al. | 606/69 |
| 6,273,899 B1 | 8/2001 | Kramer | |
| 6,290,703 B1 * | 9/2001 | Ganem | 606/250 |
| 6,294,187 B1 | 9/2001 | Boyce et al. | |
| D449,692 S | 10/2001 | Michelson | |
| 6,306,140 B1 | 10/2001 | Siddiqui | |
| 6,322,562 B1 | 11/2001 | Wolter | |
| 6,331,179 B1 * | 12/2001 | Freid et al. | 606/279 |
| 6,361,537 B1 | 3/2002 | Anderson | |
| 6,368,322 B1 * | 4/2002 | Luks et al. | 606/308 |
| 6,383,186 B1 * | 5/2002 | Michelson | 606/69 |
| 6,398,783 B1 | 6/2002 | Michelson | |
| 6,398,786 B1 * | 6/2002 | Sesic | 606/308 |
| 6,402,756 B1 | 6/2002 | Ralph et al. | |
| 6,402,759 B1 | 6/2002 | Strong et al. | |
| 6,413,259 B1 | 7/2002 | Lyons et al. | |
| 6,416,528 B1 | 7/2002 | Michelson | |
| 6,423,068 B1 | 7/2002 | Reisberg et al. | |
| 6,428,542 B1 * | 8/2002 | Michelson | 606/70 |
| 6,440,135 B2 | 8/2002 | Orbay et al. | |
| 6,440,136 B1 | 8/2002 | Gambale et al. | |
| 6,454,769 B2 | 9/2002 | Wagner et al. | |
| 6,458,133 B1 | 10/2002 | Lin | |
| 6,503,250 B2 | 1/2003 | Paul | |
| 6,547,790 B2 | 4/2003 | Harkey, III et al. | |
| 6,572,480 B1 * | 6/2003 | Huang | 464/106 |
| 6,585,769 B1 | 7/2003 | Muhanna et al. | |
| 6,595,993 B2 * | 7/2003 | Donno et al. | 606/71 |
| 6,620,163 B1 | 9/2003 | Michelson | |
| 6,645,208 B2 | 11/2003 | Apfelbaum et al. | |
| 6,659,702 B2 * | 12/2003 | Kitayama et al. | 411/546 |
| 6,669,701 B2 | 12/2003 | Steiner et al. | |
| 6,689,134 B2 | 2/2004 | Ralph et al. | |
| 6,702,817 B2 | 3/2004 | Beger et al. | |
| 6,709,686 B1 | 3/2004 | Matthew | |
| 6,719,759 B2 | 4/2004 | Wagner et al. | |
| 6,729,211 B1 * | 5/2004 | Snow | 81/177.75 |
| 6,730,091 B1 | 5/2004 | Pfefferle et al. | |
| 6,761,719 B2 | 7/2004 | Justis et al. | |
| 6,767,351 B2 * | 7/2004 | Orbay et al. | 606/287 |
| 6,786,909 B1 | 9/2004 | Dransfeld et al. | |
| 6,893,444 B2 | 5/2005 | Orbay | |
| 6,916,320 B2 | 7/2005 | Michelson | |
| 6,964,664 B2 * | 11/2005 | Freid et al. | 606/281 |
| 7,001,389 B1 * | 2/2006 | Navarro et al. | 606/71 |
| 7,172,600 B2 * | 2/2007 | Beger et al. | 606/104 |
| 7,220,263 B2 * | 5/2007 | Cordaro | 606/69 |
| 2001/0012940 A1 | 8/2001 | Tunc | |
| 2002/0016595 A1 * | 2/2002 | Michelson | 606/73 |
| 2002/0045896 A1 * | 4/2002 | Michelson | 606/61 |
| 2002/0045898 A1 * | 4/2002 | Freid et al. | 606/61 |
| 2002/0065517 A1 | 5/2002 | Paul | |
| 2002/0077630 A1 | 6/2002 | Lin | |
| 2002/0120268 A1 | 8/2002 | Berger | |
| 2002/0120273 A1 | 8/2002 | Needham et al. | |
| 2002/0183755 A1 | 12/2002 | Michelson | |
| 2003/0018335 A1 * | 1/2003 | Michelson | 606/61 |
| 2003/0044257 A1 * | 3/2003 | Siegel et al. | 411/402 |
| 2003/0105462 A1 * | 6/2003 | Haider | 606/69 |
| 2003/0153919 A1 | 8/2003 | Harris | |
| 2003/0208204 A1 * | 11/2003 | Bailey et al. | 606/69 |
| 2004/0039387 A1 | 2/2004 | Gause et al. | |
| 2004/0044345 A1 | 3/2004 | DeMoss et al. | |
| 2004/0068319 A1 * | 4/2004 | Cordaro | 623/17.11 |
| 2004/0073218 A1 | 4/2004 | Dahners | |
| 2004/0153092 A1 * | 8/2004 | Beger et al. | 606/104 |
| 2004/0181228 A1 | 9/2004 | Wagner et al. | |
| 2004/0236332 A1 | 11/2004 | Frigg | |
| 2004/0260291 A1 | 12/2004 | Jensen | |

\* cited by examiner

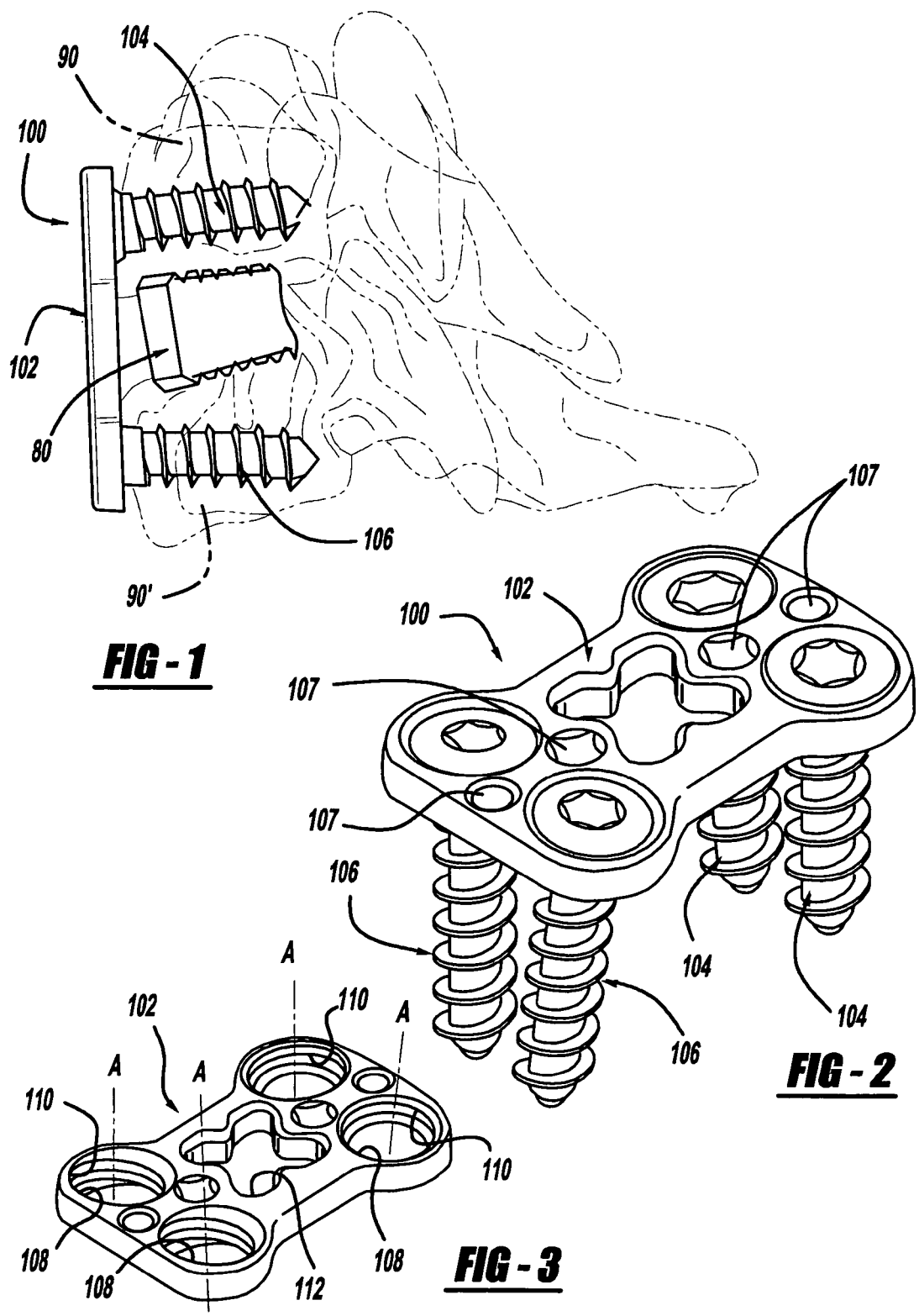

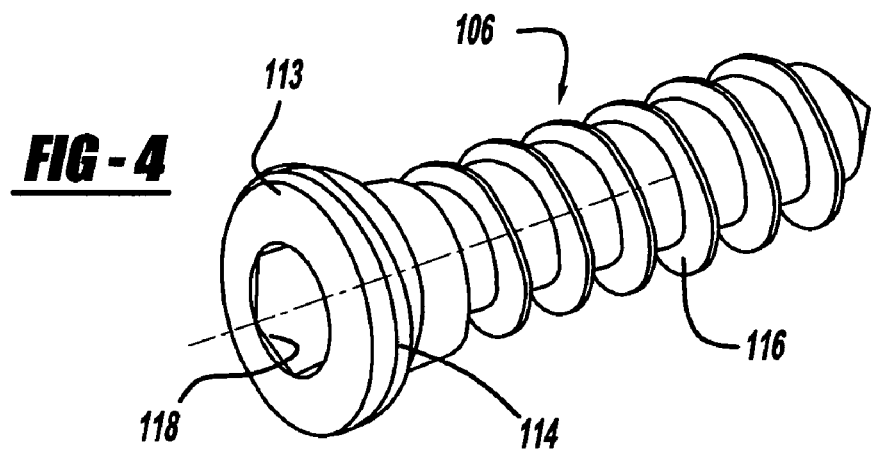
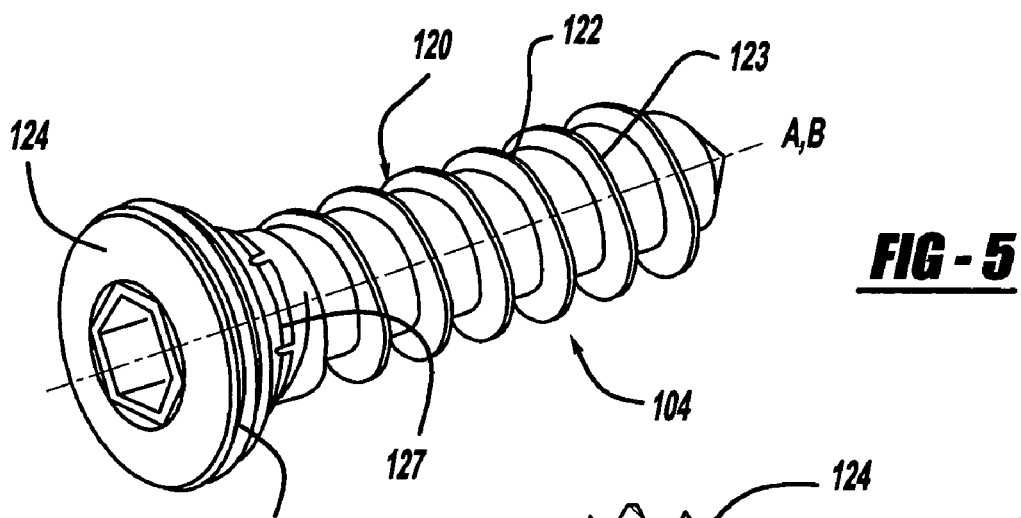
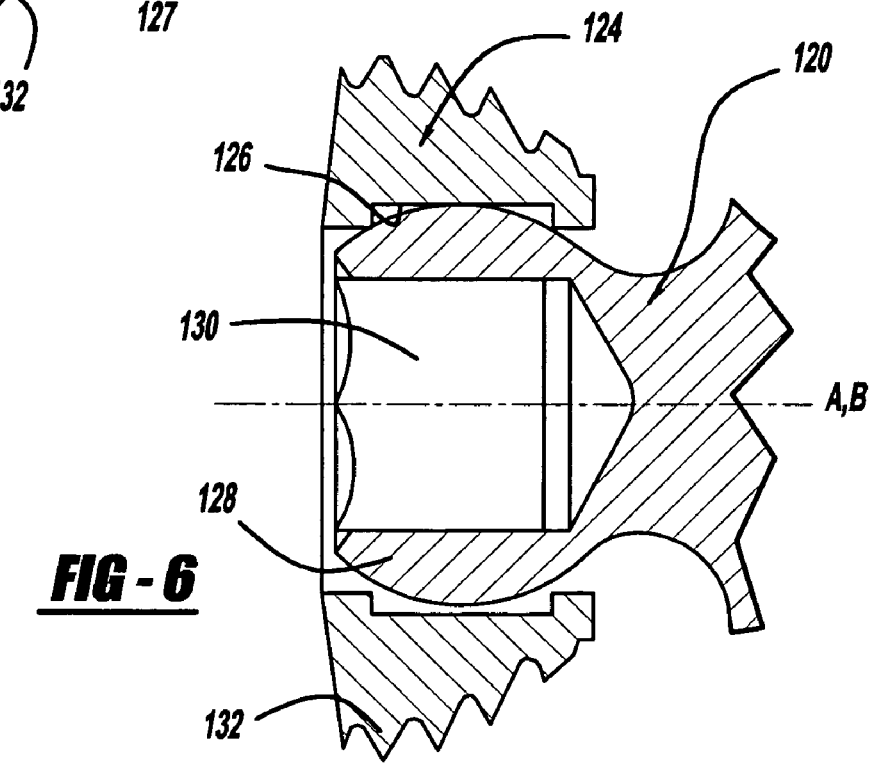

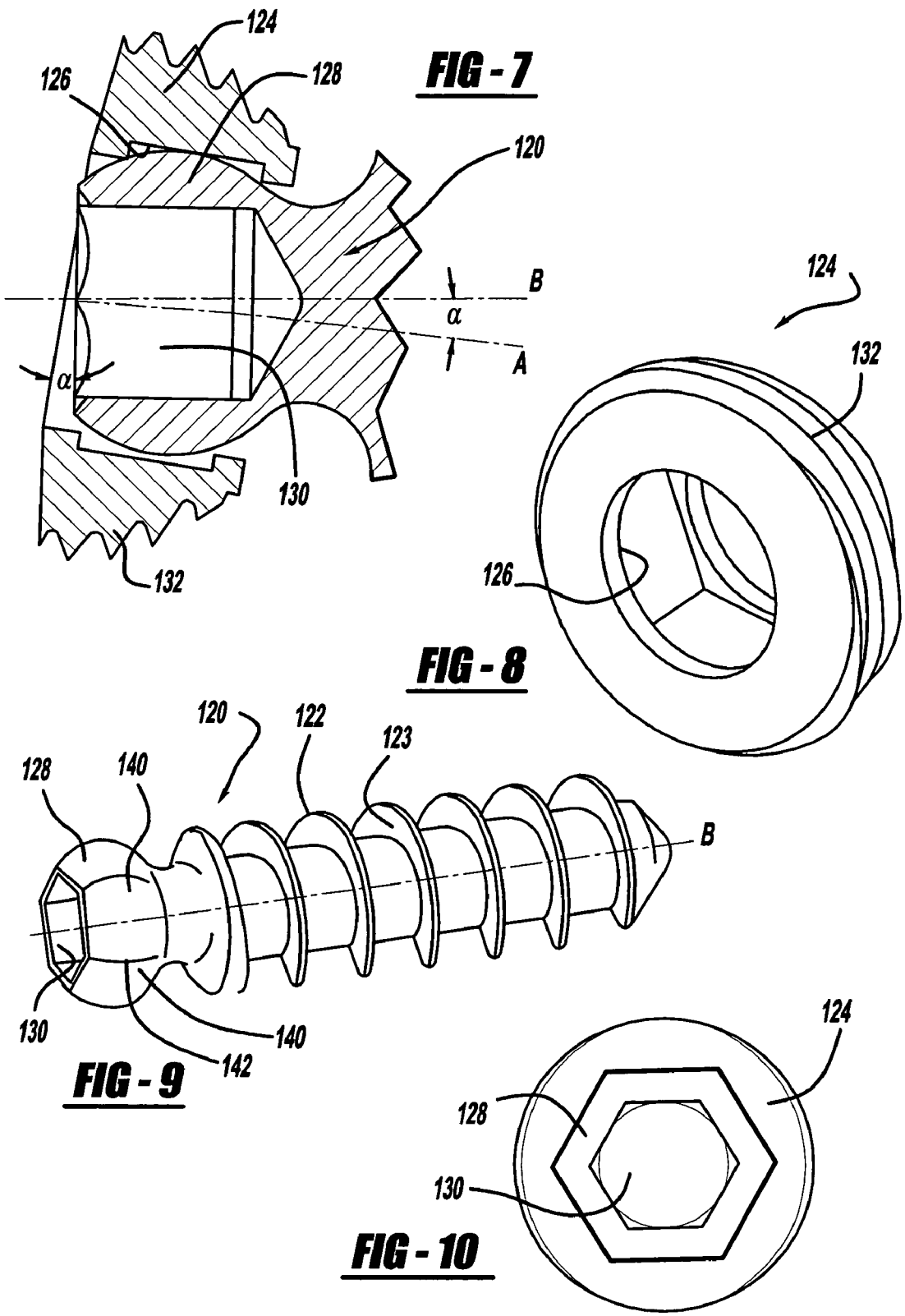

BONE FIXATION SYSTEM

INTRODUCTION

In certain orthopedic surgical procedures, it is necessary to secure multiple bones or bone portions relative to each other. For example, in certain spinal surgeries, the fusion of two or more vertebral bodies is required to secure a portion of the spinal column in a desired position. This need may be the result of physical trauma from fractures or dislocations, degenerative diseases, or tumors.

One such spinal fixation procedure involves the attachment of a prosthesis or plate to the anterior side of the cervical portion of the spine. The procedure requires anteriorly accessing the spine and securing a prosthetic plate to two or more cervical vertebrae. This allows fusion of the two or more cervical vertebrae in a particular orientation so to facilitate healing or to alleviate a condition of the patient.

Various fusion plates and plating systems are known for anteriorly fusing the cervical spine. Such plates and plating systems must meet several requirements that often are in conflict. For example, the requirements associated with spinal stability and system reliability over an extended period of use often conflict with the requirements of an easy to use implant. Strength requirements for a fusion plate tend to make the plate bulky and adversely effect intra-operative and post-operative viewing of the associate area of the spine. Additionally, it is desirable that the affected region of the cervical spine be easily viewed using MRI or x-ray procedures to verify that the desired fusion of the cervical spine is complete and/or that the alignment of the cervical vertebrae is proper.

It is further desirable to ensure that the bone screws placed into the vertebrae through the plating system do not loosen or back out from the plate. Furthermore, locking mechanisms should adequately permit the removal of an associated bone screw when required, and allow sufficient angular freedom for bone screws relative to a plate.

It remains desirable in the pertinent art to provide an improved anterior cervical plating system that addresses all the requirements discussed above.

SUMMARY

The present teachings provide a bone fixation system. In one aspect, the bone fixation system includes a fixation plate including at least one fixation hole, and at least one fastener. The fastener includes a coupler and a shank for engaging a bone. The coupler is threadably engaged with the fixation hole and the shank is angulatably retained by the coupler and orientable relative to the fixation plate at a selectable angle.

In another aspect, the bone fixation system includes a fixation plate including at least one hole therethrough defining a center axis substantially perpendicular to the fixation plate, and an angulatable fastener insertable in the hole. The angulatable fastener includes a shank having a bone engagement portion, and a coupler for coupling the shank to the hole of the fixation plate. The shank is retained by the coupler and prevented from rotating about the center axis relative to the coupler. The shank can angulate relative to the coupler about at least one axis orthogonal to the center axis.

In another aspect, the bone fixation system can include a fixation plate having a viewing window and a plurality of fastener-receiving threaded holes, at least one non-angulatable fastener threadably couplable to the fixation plate, and at least one angulatable fastener threadably couplable to the fixation plate. The angulatable fastener comprises a coupler and a shank retained by the coupler. The coupler is threadable to the fixation plate, and the shank is angulatable relative to the coupler.

The present teachings also provide a method of surgically repairing bone with a fixation plate having at least one fixation hole. The method includes providing at least one fastener having a shank and a coupler, the shank angulatably retained by the coupler, threadably engaging the coupler with the fixation hole for preventing back out of the fastener from the fixation hole, and angulating the shank relative to the coupler for orienting the fastener at a selectable angle relative to the fixation plate.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is an isometric environmental view of a bone fixation system according to the present teachings, the bone fixation system shown operatively associated with first and second vertebral bodies of a human spine;

FIG. 2 is an isometric view of the bone fixation system of FIG. 1;

FIG. 3 is an isometric view of a fixation plate for the bone fixation system of FIG. 1;

FIG. 4 is an isometric view of a non-angulatable fastener of the bone fixation system of FIG. 1;

FIG. 5 is an isometric view of an angulatable fastener of the bone fixation system of FIG. 1;

FIG. 6 is a sectional view of the angulatable fastener of FIG. 5 shown in a non-angulating position;

FIG. 7 is a sectional view of the angulatable fastener of FIG. 5 shown in an angulating position;

FIG. 8 is an isometric view of a coupler of the angulatable fastener of FIG. 5;

FIG. 9 is an isometric view of a shank of the angulatable fastener of FIG. 5; and FIG. 10 is a sectional view of the angulatable fastener of FIG. 5, shown in a non-angulating position.

DETAILED DESCRIPTION

The following description is merely exemplary in nature and is in no way intended to limit the invention, its application, or uses. For example, although the present teachings are illustrated for internal fixation of the cervical spine, the present teachings can also be used for other orthopedic procedures in which it is necessary to secure two bone portions relative to one another.

Referring to FIG. 1, an exemplary bone fixation system 100 according to the present teachings is illustrated as implanted in the anterior cervical spine for securing two cervical vertebrae 90, 90' relative to one another, without interfering with any bone graft 80, which may also be implanted therebetween.

Referring to FIGS. 2-5, the bone fixation system 100 can include a fixation plate 102, and a plurality of fixation fasteners, including angulatable (semi-constrained) fixation fasteners 104 and non-angulatable (constrained) fixation fasteners 106. As used herein, the term "constrained" is intended to mean fixed in angular orientation. The term "semi-constrained" is intended to mean having a variable angle of angulation for orientation within a cone of angulation.

The fixation plate 102 can include a large viewing window 112, which allows graft visualization during surgery, and also in postoperative X-ray and MRI diagnostic procedures. The fixation plate 102 can also include a plurality of fixation holes 108 having threads 110 for interchangeably receiving the semi-constrained and/or constrained fixation fasteners 104, 106. The fixation fasteners 104, 106 can include self-tapping and/or self-drilling bone engaging portions. Although the fixation plate 102 is illustrated with four fixation holes 108 pairwise arranged in two fixation levels for fixation of two bone portions, it will be appreciated that the fixation plate 102 can include additional fixation holes and corresponding fixation levels for fixation of three or more bone portions. Each fixation hole 108 defines a center axis A which is substantially perpendicular to the fixation plate 102.

Referring to FIG. 4, the constrained fixation fastener 106 can include a bone engaging portion 116 which can be threaded, and a head 113. The head 113 can include an interior hex recess or other driver-receiving formation 118 to facilitate inserting the constrained fixation fastener 106 into the bone through one of the fixation holes 108 of the fixation plate 102. The hex recess 118 can also be engaged by a driver to remove the fixation fastener 106 from the fixation plate 102. The head 113 can also include external threads 114 for engaging the threads 110 of the fixation hole 108 to prevent backing out of the constrained fixation fastener 106 after implantation. The constrained fixation fastener 106, once threaded into the fixation plate 102, remains in a fixed orientation. In the embodiment illustrated in FIG. 4, the longitudinal axis of the constrained fixation fastener 106 coincides with the center axis A of the fixation hole 108 and is substantially perpendicularly to the fixation plate 102.

Referring to FIGS. 5-10, the semi-constrained fixation fastener 104 includes a shank 120 and a coupler 124. The shank 120 defines a longitudinal axis B and has a bone-engaging portion 122 with threads 123, and a coupler-engaging portion, such as a ball hex 128. The ball hex 128 includes six spherical or curved portions 140 interconnected at ridges 142. The ball hex 128 can also include a driver-receiving recess, such as a hex recess 130. The coupler 124 can include external threads 132 engaging the threads 110 of the fixation hole 108 of the fixation plate 102 for preventing backing out of the semi-constrained fixation fastener 104 after implantation. When the coupler 124 is engaged with the fixation hole 108, the coupler's center axis coincides with the center axis A of the hole. The coupler 124 also includes a prismatic hex opening 126 which receives and retains the ball hex 128, and allows the shank 120 to angulate relative to the coupler 124, as illustrated in FIG. 7. The shank 120 can be non-removably retained in the coupler 124 by crimping a retaining portion 127 of the coupler 124 around the shank 120, as shown in FIG. 5. It will be appreciated that other known retaining devices can be used to the same effect.

Referring to FIGS. 5 and 6, the coupler 124 and the shank 120 can rotate as an integral unit about the center axis A, without relative rotation between the shank 120 and the ball hex 128 about the center axis A, by using a driver that engages the recess 130 of the ball hex 128. The shank 120 can angulate about the ball hex 128 by rotating relative to the ball hex 128 about axes that are orthogonal to the center axis A, as illustrated in FIG. 7. In the angulated position, the center axis A and the longitudinal axis B of the shank define an angle α. In this manner, the shank 120 can rotate relative to the fixation plate 102 within a cone of angulation that is defined by the maximum angle α that can be accommodated by the geometry of the semi-constrained fixation fastener 104. For example, the angle α can take values ranging from 0° to 30°, although other angle ranges are possible.

The fixation plate 102 and the fixation fasteners 104, 106 can be made of biocompatible materials, including, but not limited to, titanium, titanium alloys, such a Ti-6Al-4V, for example, or other materials.

Referring to FIGS. 1, 2 and 3, in a cervical fixation procedure, the fixation plate 102 can be provisionally secured to the vertebrae 80 using bone pins through small holes 107 of the fixation plate 102. One or more constrained fixation fasteners 106 can be threaded into corresponding fixation holes 108 of the fixation plate 102 and implanted into a first bone portion or vertebra 90. One or more semi-constrained fixation fasteners 104 can be threaded into corresponding fixation holes 108 of the fixation plate 102 and implanted into a second bone portion or vertebra 90'. The semi-constrained fixation fasteners 104 can be angulated within a cone of angulation relative to the fixation plate 102. It will be appreciated that the fixation plate 102 can be used with any combination of constrained and semi-constrained fixation fasteners 106, 104, including all constrained fixation fasteners 106 or all semi-constrained fixation fasteners 104.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A bone fixation system comprising:
   a fixation plate including at least one fixation hole; and
   at least one fastener, the fastener including a coupler and a shank for engaging a bone, the coupler threadably engaged with the fixation hole, and the shank angulatably retained by the coupler and orientable relative to the fixation plate at a selectable angle, wherein the shank includes a ball hex portion retained by a hex aperture of the coupler, the ball hex portion including six curved portions connected to one another with ridges, the ball hex including a driver engagement recess for rotating the shank and the coupler together relative to the fixation plate without rotating the shank relative to the coupler and for threading the coupler to the fixation hole.

2. The bone fixation system of claim 1, wherein the shank has a longitudinal axis movable within a cone of angulation relative to a center axis of the fixation hole.

3. A bone fixation system comprising:
   a fixation plate including at least one hole therethrough defining a center axis substantially perpendicular to the fixation plate; and
   an angulatable fastener insertable in the hole, the angulatable fastener comprising:
      a shank having a bone engagement portion; and
      a coupler for coupling the shank to the hole of the fixation plate, wherein the shank is retained by the coupler and prevented from rotating about the center axis relative to the coupler, and wherein the shank can angulate relative to the coupler about at least one axis orthogonal to the center axis, wherein the shank comprises a ball hex received in a prismatic hex opening of the coupler, the ball hex portion including six curved portions connected to one another with ridges, the ball hex including a hex recess for receiving a driver for rotating the shank and the coupler together relative to the fixation plate without rotating the shank relative to the coupler.

4. The bone fixation system of claim 3, wherein the coupler comprises external threads for engaging the hole of the fixation plate.

5. The bone fixation system of claim 3, further comprising a non-angulatable fastener receivable in another hole defined in the fixation plate.

6. The bone fixation system of claim 3, wherein the shank is retained in the coupler by crimping a retaining portion of the coupler around the shank.

7. A bone fixation system comprising:
- a fixation plate having a viewing window and a plurality of fastener-receiving threaded holes;
- at least one non-angulatable fastener threadably couplable to the fixation plate; and
- at least one angulatable fastener threadably couplable to the fixation plate, wherein the angulatable fastener comprises a coupler and a shank retained by the coupler, wherein the coupler is threadable to the fixation plate, and the shank is angulatable relative to the coupler, wherein the shank includes a ball hex portion coupled to a hex opening of the coupler, the ball hex portion including six curved portions connected to one another with ridges, the ball hex portion including a hex recess for receiving a driver for rotating the shank and the coupler together relative to the fixation plate without rotating the shank relative to the coupler.

8. The bone fixation device of claim 7, wherein the shank has a longitudinal axis, the longitudinal axis movable within a cone of angulation relative to the coupler.

9. A bone fixation system comprising:
- a fixation plate having a threaded hole;
- a coupler having an outer threaded surface threadably engaged with the threaded hole, the coupler defining a prismatic hex aperture;
- a shank having a bone engagement portion and a ball hex portion, the ball hex portion retained by the prismatic hex aperture of the coupler, the ball hex portion including six curved portions connected to one another with ridges, the shank angulatable relative to the coupler within a cone of angulation centered around an axis perpendicular to the fixation plate, the ball hex portion including a driver recess for rotating the shank and the coupler together relative to the fixation plate without rotating the shank relative to the coupler.

* * * * *